(12) United States Patent
Hosokawa et al.

(10) Patent No.: US 7,357,991 B2
(45) Date of Patent: Apr. 15, 2008

(54) SOLUBLE COMPOUND AND ORGANIC ELECTROLUMINESCENT DEVICES

(75) Inventors: Chiushio Hosokawa, Sodegaura (JP); Masakazu Funahashi, Sodegaura (JP); Hidetsugu Ikeda, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 113 days.

(21) Appl. No.: 10/493,236

(22) PCT Filed: Oct. 29, 2002

(86) PCT No.: PCT/JP02/11192

§ 371 (c)(1),
(2), (4) Date: Apr. 21, 2004

(87) PCT Pub. No.: WO03/037836

PCT Pub. Date: May 8, 2003

(65) Prior Publication Data

US 2005/0014017 A1    Jan. 20, 2005

(30) Foreign Application Priority Data

Oct. 31, 2001  (JP) ............................. 2001-334324

(51) Int. Cl.
 *H01J 1/62* (2006.01)

(52) U.S. Cl. ........................ 428/690; 428/917; 313/504; 313/506; 257/40; 257/103; 252/301.35; 252/301.16

(58) Field of Classification Search ................. 428/690; 429/917; 313/504, 506; 257/E51.028, 40; 252/301.35, 301.16

See application file for complete search history.

(56) References Cited

U.S. PATENT DOCUMENTS

| | | | |
|---|---|---|---|
| 6,214,481 B1 * | 4/2001 | Sakai et al. .................. | 428/690 |
| 6,395,411 B1 | 5/2002 | Kwon et al. ................. | 428/690 |
| 6,730,419 B2 * | 5/2004 | Kim et al. .................... | 428/690 |

FOREIGN PATENT DOCUMENTS

| | | | |
|---|---|---|---|
| JP | 8-333569 | | 12/1996 |
| JP | 2000-007604 | | 1/2000 |
| JP | 2000-191560 | * | 7/2000 |

* cited by examiner

*Primary Examiner*—Milton I. Cano
*Assistant Examiner*—Camie S. Thompson
(74) *Attorney, Agent, or Firm*—Steptoe & Johnson LLP

(57) ABSTRACT

A novel soluble compound which is a distyrylarylene derivative having a soluble substituent and a specific central group and having a solubility of 0.5% by weight or greater at 20° C. in an organic solvent; and an organic electroluminescence device having an organic thin film layer which has a single layer or a plurality of layers, is disposed between a cathode and an anode and has at least one layer containing the novel soluble compound. The organic thin film layer can be formed in accordance with a wet process, and the organic electroluminescence device exhibiting a great efficiency of light emission can be produced easily.

12 Claims, No Drawings

SOLUBLE COMPOUND AND ORGANIC ELECTROLUMINESCENT DEVICES

TECHNICAL FIELD

The present invention relates to a novel soluble compound and organic electroluminescence devices and, more particularly, to a novel soluble compound which can be formed into an organic thin film layer in accordance with a wet process and enables producing electroluminescence devices exhibiting a great efficiency of light emission easily and an electroluminescence device utilizing the compound.

BACKGROUND ART

An organic electroluminescence (electroluminescence will be referred to as EL, hereinafter) is a spontaneous light emitting device which utilizes the principle that a fluorescent substance emits light by energy of recombination of holes injected from an anode and electrons injected from a cathode when an electric field is applied.

Since an organic EL device of the laminate type driven under a low electric voltage was reported by C. W. Tang of Eastman Kodak Company (C. W. Tang and S. A. Vanslyke, Applied Physics Letters, Volume 51, Pages 913, 1987), many studies have been conducted on organic EL devices using organic materials as the constituting materials. Tang et al. used a laminate structure using tris(8-hydroxyquinolinol) aluminum for the light emitting layer and a triphenyldiamine derivative for the hole transporting layer. Advantages of the laminate structure are that the efficiency of hole injection into the light emitting layer can be increased, that the efficiency of forming excitons which are formed by blocking and recombining electrons injected from the cathode can be increased, and that excitons formed within the light emitting layer can be enclosed. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

As the light emitting material, chelate complexes such as tris(8-quinolinolato)aluminum, coumarine derivatives, tetraphenyl-butadiene derivatives, bisstyrylarylene derivatives and oxadiazole derivatives are known. It is reported that light in the visible region ranging from blue light to red light can be obtained by using these light emitting materials, and development of a device exhibiting color images is expected (For example, Japanese, Patent Application Laid-Open Nos. Heisei 8(1996)-239655, Heisei 7(1995)-138561 and Heisei 3(1991)-200889.

Devices using anthracene derivatives as the hole transporting material or the light emitting material are disclosed in Japanese Patent No. 3175816. However, although an excellent device emitting blue light can be made by using the anthracene derivatives, an ink in which the anthracene derivatives are dissolved cannot be prepared since the used compounds are not easily soluble in solvents. The device cannot be produced in accordance with a wet process such as the spin coating process, the printing process and the ink-jet process and is produced in accordance with the vacuum vapor deposition process. Therefore, a compound which can be easily formed into a film in accordance with a wet process, which does not require vacuum, and a device using the compound have been desired.

On the other hand, in Japanese Patent Application Laid-Open No. 2000-143569, a distyryl compound having a soluble substituent is disclosed. However, this compound has a poor light emitting property since this compound does not have the anthracene nucleus or the fluorene nucleus as the central group, and the improvement has been desired.

DISCLOSURE OF THE INVENTION

The present invention has been made to overcome the above drawbacks and has an object of providing a novel soluble compound which can be formed into an organic thin film layer in accordance with a wet process and enables producing electroluminescence devices exhibiting a great efficiency of light emission easily and an electroluminescence device utilizing the compound.

As the result of intensive studies by the present inventors to overcome the above drawbacks, it was found that the above drawbacks could be overcome by using a distyrylarylene derivative which is soluble in organic solvents and has a specific central group as the material of the organic thin film layer. The present invention has been completed based on this knowledge.

The present invention provides a novel soluble compound which is a distyrylarylene derivative represented by general formula (1) and has a solubility (20° C.) of 0.5% by weight or greater in an organic solvent, general formula (1) being:

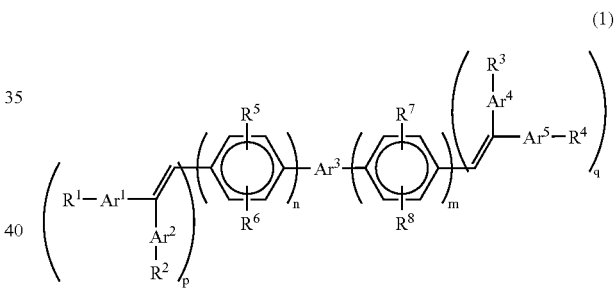

wherein $Ar^1$, $Ar^2$, $Ar^4$ and $Ar^5$ each independently represent a substituted or unsubstituted phenylene group, a substituted or unsubstituted naphthalene group, a substituted or unsubstituted anthracene group, a substituted or unsubstituted diphenylanthracene group, a substituted or unsubstituted phenanthrene group, a substituted or unsubstituted acenaphthene group, a substituted or unsubstituted biphenylene group, a substituted or unsubstituted fluorene group, a substituted or unsubstituted carbazolyl group, a substituted or unsubstituted thiophene group, a substituted or unsubstituted triazole group or a substituted or unsubstituted thiadiazole group;

$R^1$ to $R^4$ each independently represent hydrogen atom, an alkyl group having 1 to 20 carbon atoms, an alkoxyl group having 1 to 20 carbon atoms, an aryl group having 6 to 20 carbon atoms, a trialkylsilyl group having 3 to 20 carbon atoms or cyano group;

$Ar^3$ represents a substituted or unsubstituted anthracendiyl group or a substituted or unsubstituted fluorendiyl group;

$R^5$ to $R^8$ each independently represent hydrogen atom, a halogen atom, hydroxyl group, a substituted or unsubstituted amino group, nitro group, cyano group, a substituted or unsubstituted alkyl group having 1 to 30 carbon atoms, a substituted or unsubstituted alkenyl group having 2 to 30 carbon atoms, a substituted or unsubstituted cycloalkyl group having 5 to 30 carbon atoms, a substituted or unsubstituted alkoxyl group having 1 to 30 carbon atoms, a substituted or unsubstituted aromatic hydrocarbon group having 6 to 30 carbon atoms, a substituted or unsubstituted aromatic heterocyclic group having 2 to 30 carbon atoms, a substituted or unsubstituted aralkyl group having 7 to 30 carbon atoms, a substituted or unsubstituted aryloxyl group having 6 to 30 carbon atoms, a substituted or unsubstituted alkoxycarbonyl group having 2 to 30 carbon atoms or carboxyl group, groups represented by $R^6$ and $R^5$ or $R^7$ and $R^8$ may be bonded to each other and form a cyclic structure which may have substituents;

p represents 0 or 1, q represents 0 or 1, m represents 0 or an integer of 1 to 3, and n represents an integer of 1 to 3.

It is sufficient that at least one organic solvent which dissolves 0.5% by weight or more of the novel soluble compound at 20° C. exists.

The present invention also provides an organic electroluminescence device which comprises a cathode, an anode and an organic thin film layer comprising a single layer or a plurality of layers and disposed between the cathode and the anode, wherein at least one layer in the organic thin film layer comprises a novel soluble compound described above.

THE MOST PREFERRED EMBODIMENT TO CARRY OUT THE INVENTION

In the present invention, the soluble compound is a compound which has a soluble substituent, is represented by general formula (1) shown above and has a solubility (20° C.) of 0.5% by weight or greater in an organic solvent. It is sufficient that at least one organic solvent which dissolves 0.5% by weight or more of the novel soluble compound at 20° C. exists.

It is preferable that the organic solvent is at least one solvent selected from toluene, xylene, N-methylpyrrolidone, γ-butyrolactone, 1,3-dimethyl-2-imidazoline, carbitol acetate, butylcarbitol acetate, dichloromethane, dichloroethane, chlorobenzene tetralin and alcohols having 1 to 10 carbon atoms, and more preferably dichloroethane, toluene, xylene or tetraline.

In general formula (1) shown above, $Ar^1$, $Ar^2$, $Ar^4$ and $Ar^5$ each independently represent a substituted or unsubstituted phenylene group, a substituted or unsubstituted naphthalene group, a substituted or unsubstituted anthracene group, a substituted or unsubstituted diphenylanthracene group, a substituted or unsubstituted phenanthrene group, a substituted or unsubstituted acenaphthene group, a substituted or unsubstituted biphenylene group, a substituted or unsubstituted fluorene group, a substituted or unsubstituted carbazolyl group, a substituted or unsubstituted thiophene group, a substituted or unsubstituted triazole group or a substituted or unsubstituted thiadiazole group.

In general formula (1) shown above, $R^1$ to $R^4$ each independently represent hydrogen atom, an alkyl group having 1 to 20 carbon atoms, an alkoxyl group having 1 to 20 carbon atoms, an aryl group having 6 to 20 carbon atoms, a trialkylsilyl group having 3 to 20 carbon atoms or cyano group.

Examples of the alkyl group having 1 to 20 carbon atoms include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

The alkoxyl group having 1 to 20 carbon atoms is a group represented by —OY. Examples of the group represented by Y include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

Examples of the aryl group having 6 to 20 carbon atoms include phenyl group, naphthyl group, anthryl group, phenanthryl group, naphthacenyl group and pyrenyl group. Examples of the substituent to the aryl group include halogen atoms, hydroxyl group, substituted and unsubstituted amino groups described above, nitro group, cyano group, substituted and unsubstituted alkyl groups described above, substituted and unsubstituted alkenyl groups described above, substituted and unsubstituted cycloalkyl groups described above, substituted and unsubstituted alkoxyl groups described above, substituted and unsubstituted aromatic hydrocarbon groups described above, substituted and unsubstituted aromatic heterocyclic groups described above, substituted and unsubstituted aralkyl groups described above, substituted and unsubstituted aryloxyl groups described above, substituted and unsubstituted alkoxycarbonyl groups described above and carboxyl group.

Examples of the trialkylsilyl group having 3 to 20 carbon atoms in include trimethylsilyl group, triethylsilyl group, tripropylsilyl group, tributylsilyl group, tripentyl silyl group and trihexylsilyl group.

In general formula (1) shown above, $Ar^3$ represents a substituted or unsubstituted anthracendiyl group or a substituted or unsubstituted fluorendiyl group.

It is preferable that $Ar^3$ represents:
anthracendiyl group or fluorendiyl group having at least one group selected from:
(1) linear and branched alkyl groups having 5 or more carbon atoms and an olefinic unsaturated bond,
(2) linear, branched and cyclic substituted and unsubstituted alkyl groups having 4 or more carbon atoms,
(3) linear, branched and cyclic substituted and unsubstituted alkyloxyl groups having 5 or more carbon atoms,
(4) linear, branched and cyclic substituted and unsubstituted alkylthio groups having 5 or more carbon atoms,
(5) linear, branched and cyclic substituted and unsubstituted alkylsilyl groups having 5 or more carbon atoms,
(6) linear, branched and cyclic substituted and unsubstituted dialkylsilyl groups having 5 or more carbon atoms,
(7) linear, branched and cyclic substituted and unsubstituted trialkylsilyl groups having 5 or more carbon atoms,
(8) alkylamino groups and dialkylamino groups,
(9) linear and branched cyano-substituted alkyl groups having 4 or more carbon atoms and 1 or 2 cyano groups, and
(10) polyethers having 2 to 5 ether oxygen atoms which are separated from each other with an alkyl crosslinking having 1 to 3 carbon atoms, or anthracendiyl group or fluorendiyl group having a group selected from aryl groups having 6 to 30 carbon atoms, arylalkyl groups having 7 to 30 carbon atoms, heteroarylalkyl groups having at least one of nitrogen atom, oxygen atom and sulfur atom and 2 to 30 carbon atoms, heterocyclic groups having 2 to 30 carbon atoms, alkanoyl groups having 1 to 20 carbon atoms, cycloalkanoyl groups having 6 to 30 carbon atoms, aryloyl groups having 6 to 30 carbon atoms and heteroaryloxyl groups having at least one of oxygen atom and sulfur atom and 2 to 30 carbon atoms, which are substituted with at least one group selected from aforesaid (1) to (10).

It is also preferable that $Ar^3$ represents anthracendiyl group substituted with at least two substituted or unsubstituted t-butyl groups.

In general formula (1) shown above, $R^5$ to $R^8$ each independently represent hydrogen atom, a halogen atom, hydroxyl group, a substituted or unsubstituted amino group, nitro group, cyano group, a substituted or unsubstituted alkyl group having 1 to 30 carbon atoms, a substituted or unsubstituted alkenyl group having 2 to 30 carbon atoms, a substituted or unsubstituted cycloalkyl group having 5 to 30 carbon atoms, a substituted or unsubstituted alkoxyl group having 1 to 30 carbon atoms, a substituted or unsubstituted aromatic hydrocarbon group having 6 to 30 carbon atoms, a substituted or unsubstituted aromatic heterocyclic group having 2 to 30 carbon atoms, a substituted or unsubstituted aralkyl group having 7 to 30 carbon atoms, a substituted or unsubstituted aryloxyl group having 6 to 30 carbon atoms, a substituted or unsubstituted alkoxycarbonyl group having 2 to 30 carbon atoms or carboxyl group, groups represented by $R^6$ and $R^5$ or $R^7$ and $R^8$ may be bonded to each other and form a cyclic structure which may have substituents.

The amino group is represented by $-NX^1X^2$. $X^1$ and $X^2$ each independently represent hydrogen atom, methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 4-styrylphenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methyl-biphenylyl group, 4"-t-butyl-p-terphenyl-4-yl group, 2-pyrrolyl group, 3-pyrrolyl group, pyradinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methyl-pyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group or 4-t-butyl-3-indolyl group.

Examples of the alkyl group having 1 to 30 carbon atoms include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diuodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

Examples of the alkenyl group having 2 to 30 carbon atoms include vinyl group, allyl group, 1-butenyl group, 2-butenyl group, 3-butenyl group, 1,3-butadienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl-1-butenyl group and 3-phenyl-1-butenyl group.

Examples of the cycloalkyl group having 5 to 30 carbon atoms include cyclopropyl group, cyclobutyl group, cyclopentyl group, cyclohexyl group and 4-methylcyclohexyl group.

The alkoxyl group having 1 to 30 carbon atoms is represented by —OY. Examples of the group represented by Y include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

Examples of the aromatic hydrocarbon group having 6 to 30 carbon atoms include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group and 4"-t-butyl-p-terphenyl-4-yl group.

Examples of the aromatic heterocyclic group having 2 to 30 carbon atoms include 1-pyrrolyl group, 2-pyrrolyl group, 3-pyrrolyl group, pyradinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzo-furanyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methyl-pyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

Examples of the aralkyl group having 7 to 30 carbon atoms include benzyl group, 1-phenylethyl group, 2-phenylethyl group, 1-phenyl-isopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

The aryloxyl group having 6 to 30 carbon atoms is represented by —OZ. Examples of the group represented by Z include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyradinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzo-furanyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methyl-pyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

The alkoxycarbonyl group having 2 to 30 carbon atoms is represented by —COOY. Examples of the group represented by Y include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, jodomethyl group, 1-iodoethyl group, 2-jodoethyl group, 2-iodoisobutyl group, 1,2-dijodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

Examples of the divalent group forming the ring include tetramethylene group, pentamethylene group, hexamethylene group, diphenylmethane-2,2'-diyl group, diphenylethane-3,3'-diyl group and diphenylpropane-4,4'-diyl group.

It is preferable that at least one of $R^5$ to $R^8$ represents:
at least one group selected from:
(1) linear and branched alkyl groups having 5 or more carbon atoms and an olefinic unsaturated bond,
(2) linear, branched and cyclic substituted and unsubstituted alkyl groups having 4 or more carbon atoms,
(3) linear, branched and cyclic substituted and unsubstituted alkyloxyl groups having 5 or more carbon atoms,
(4) linear, branched and cyclic substituted and unsubstituted alkylthio groups having 5 or more carbon atoms,
(5) linear, branched and cyclic substituted and unsubstituted alkylsilyl groups having 5 or more carbon atoms,
(6) linear, branched and cyclic substituted and unsubstituted dialkylsilyl groups having 5 or more carbon atoms,
(7) linear, branched and cyclic substituted and unsubstituted trialkylsilyl groups having 5 or more carbon atoms,
(8) alkylamino groups and dialkylamino groups,
(9) linear and branched cyano-substituted alkyl groups having 4 or more carbon atoms and 1 or 2 cyano groups, and
(10) polyethers having 2 to 5 ether oxygen atoms which are separated from each other with an alkyl crosslinking having 1 to 3 carbon atoms, or
a group selected from aryl groups having 6 to 30 carbon atoms, arylalkyl groups having 7 to 30 carbon atoms, heteroarylalkyl groups having at least one of nitrogen atom, oxygen atom and sulfur atom and 2 to 30 carbon atoms, heterocyclic groups having 2 to 30 carbon atoms, alkanoyl groups having 1 to 20 carbon atoms, cycloalkanoyl groups having 6 to 30 carbon atoms, aryloyl groups having 6 to 30 carbon atoms and heteroaryloxyl groups having at least one of oxygen atom and sulfur atom and 2 to 30 carbon atoms, which are substituted with at least one group selected from aforesaid (1) to (10).

In general formula (1) shown above, p represents 0 or 1, q represents 0 or 1, m represents 0 or an integer of 1 to 3, and n represents an integer of 1 to 3.

Examples of the distyrylarylene derivative represented by general formula (1) of the present invention will be shown in the following. However, the distyrylarylene derivative of the present invention is not limited to the compounds shown as the examples. In the following, $C_5$ means n-pentyl group. The compounds shown in the following as the examples are all dissolved into 1,2-dichloroethane at 20° C. in an amount of 0.5% by weight or more.

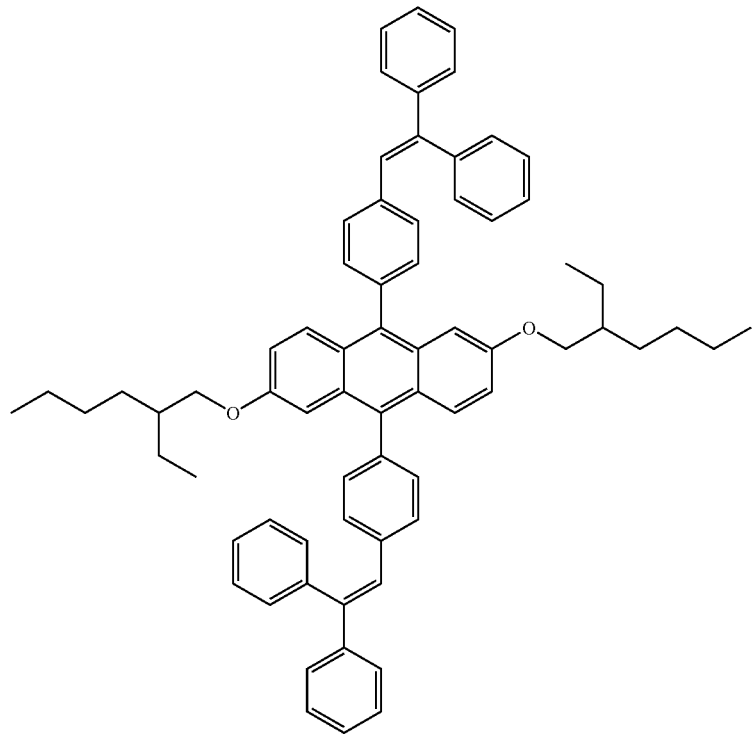
(A-1)
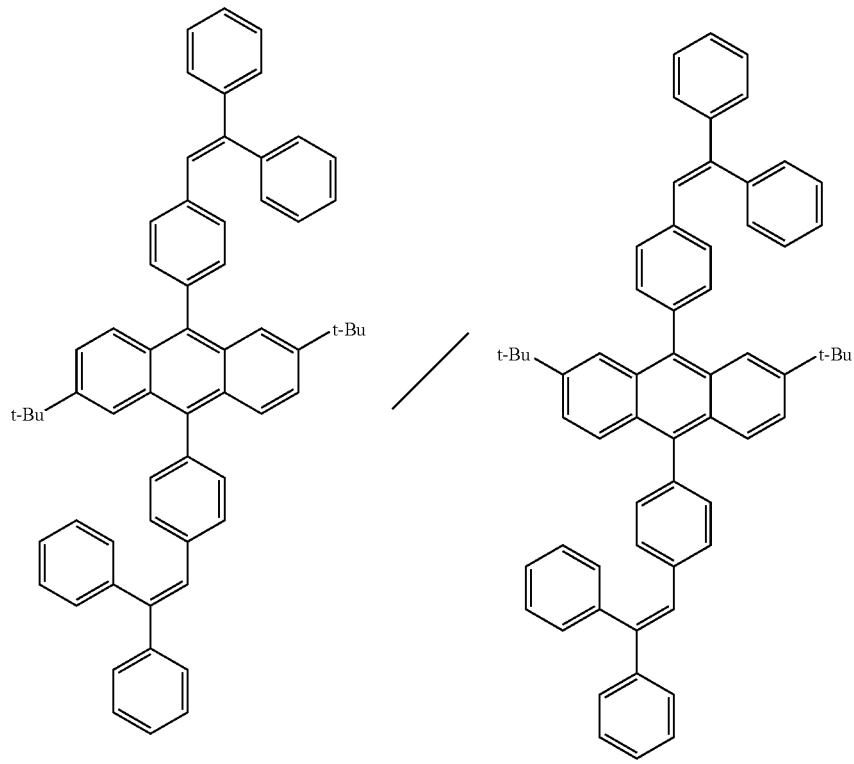
(A-2)

-continued
(A-3)
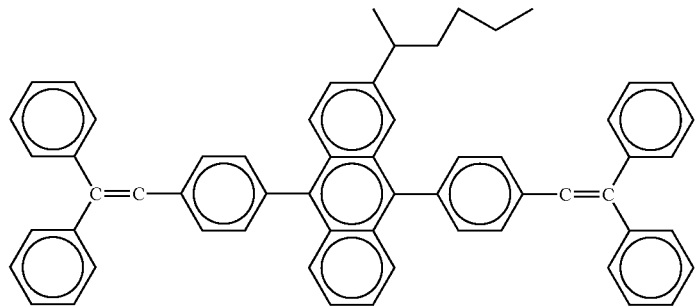
(A-4)
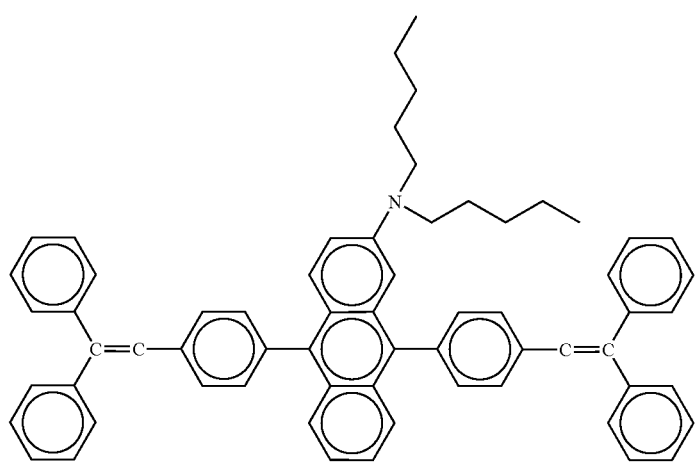
(A-5)
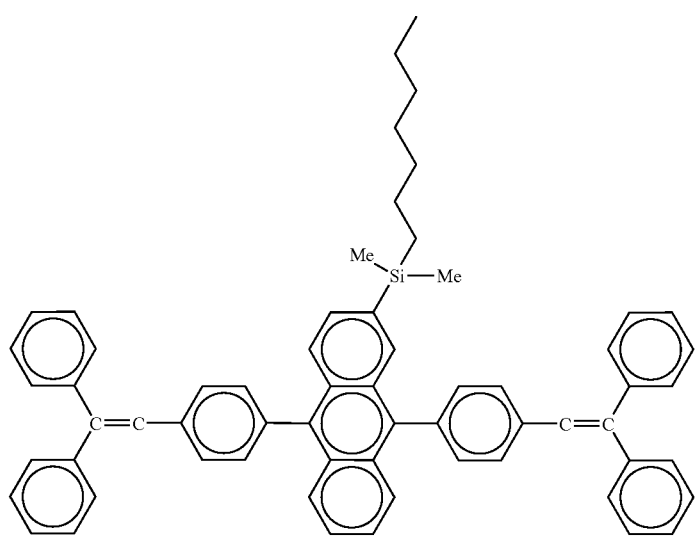

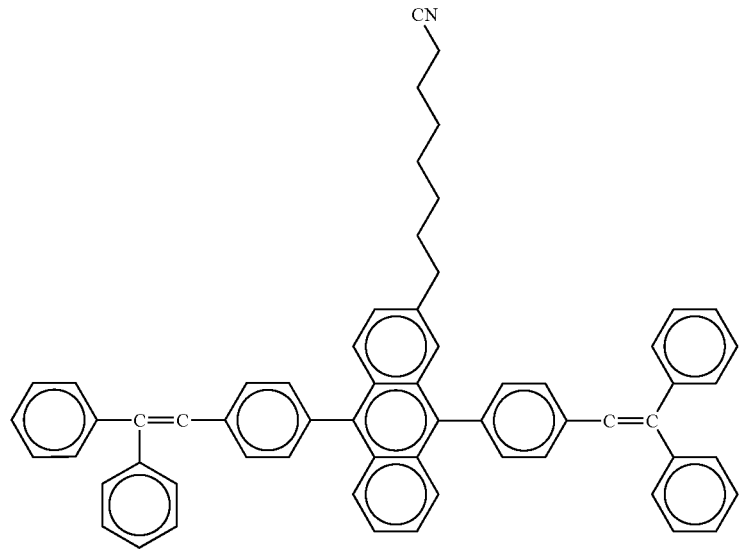
(A-6)
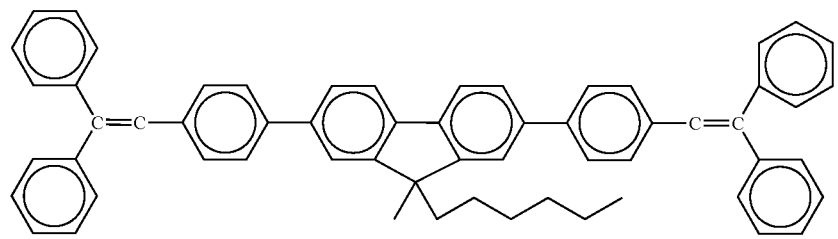
(A-7)
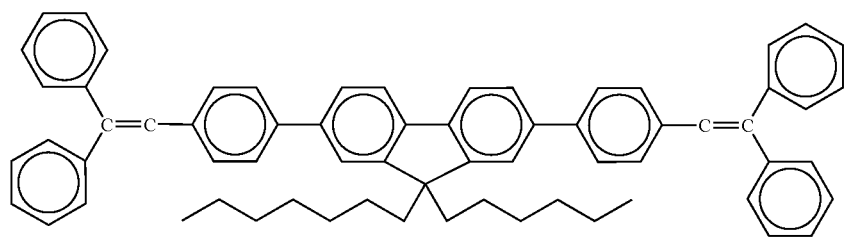
(A-8)
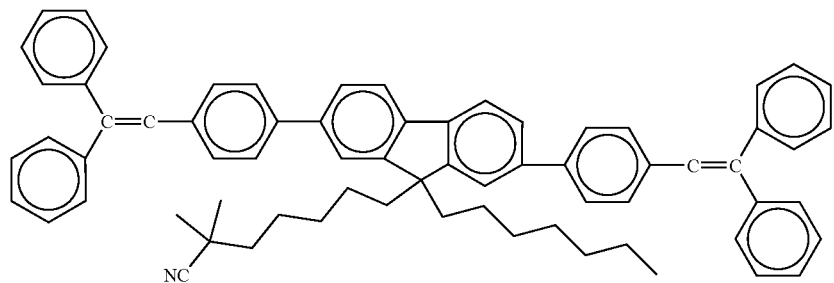
(A-9)

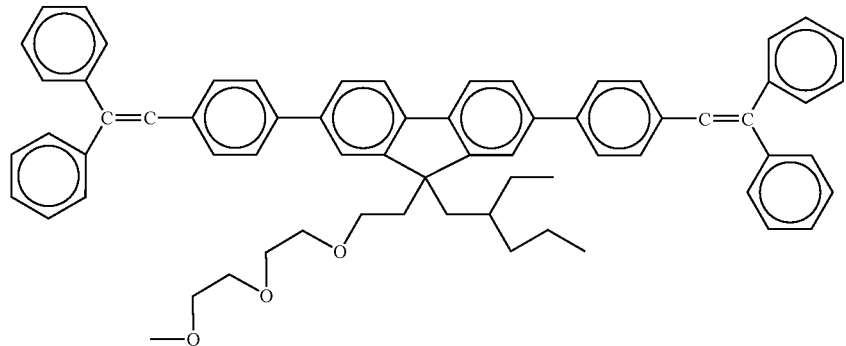
(A-10)
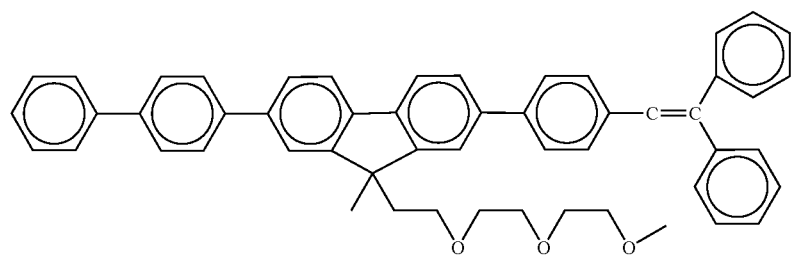
(A-11)
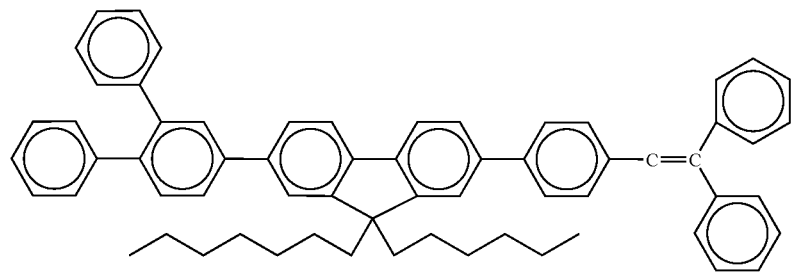
(A-12)
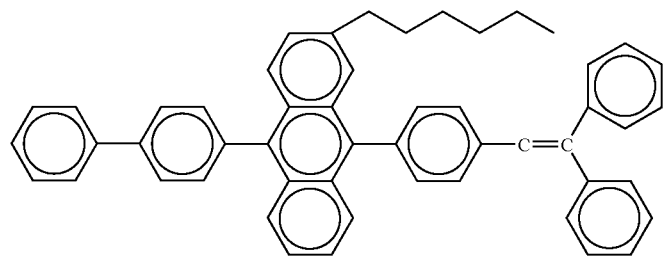
(A-13)
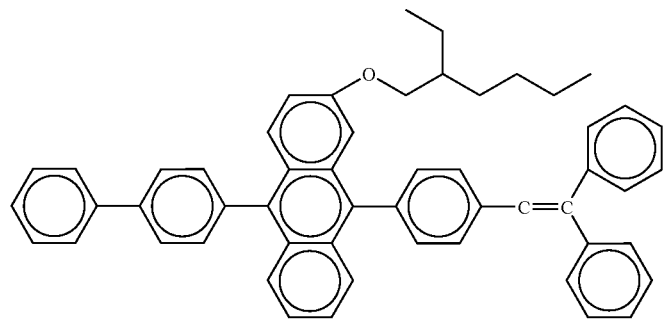
(A-14)

(A-15)
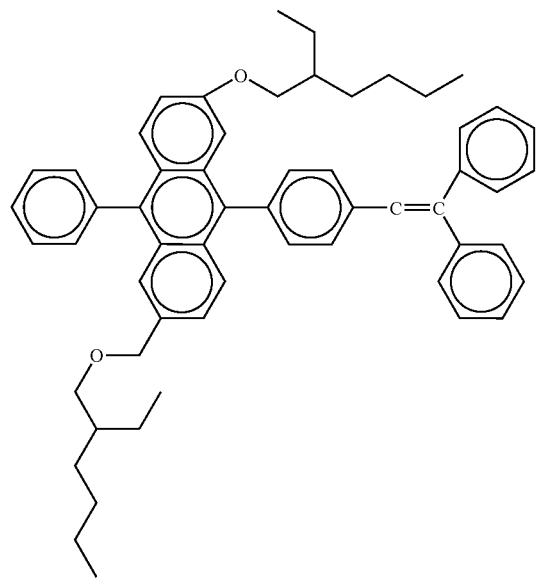
(A-16)
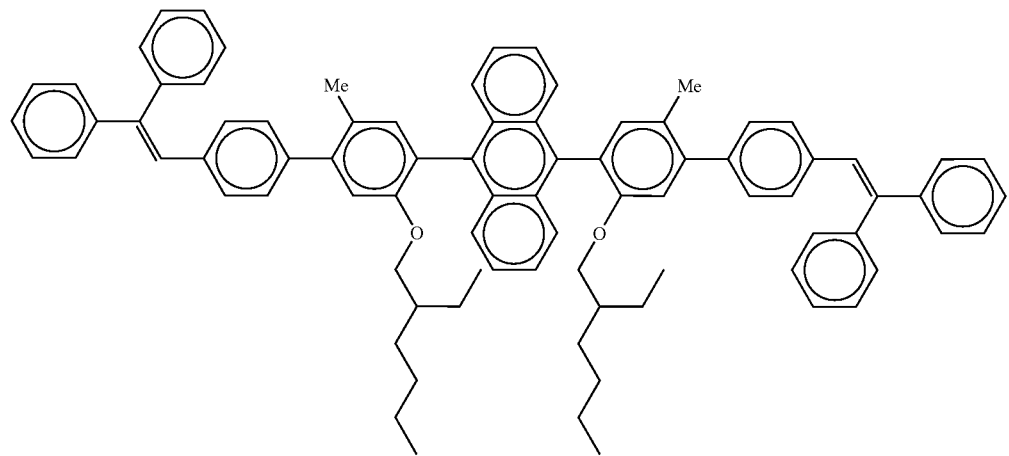
(A-17)
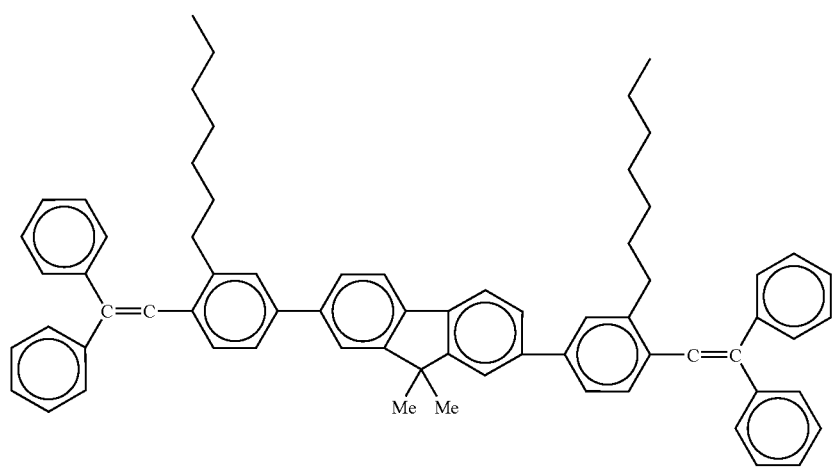

-continued
(A-18)
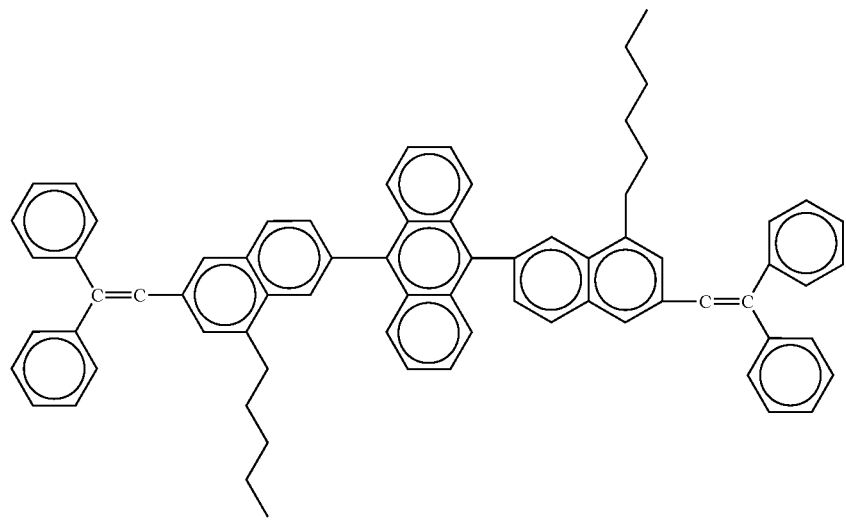
(A-19)
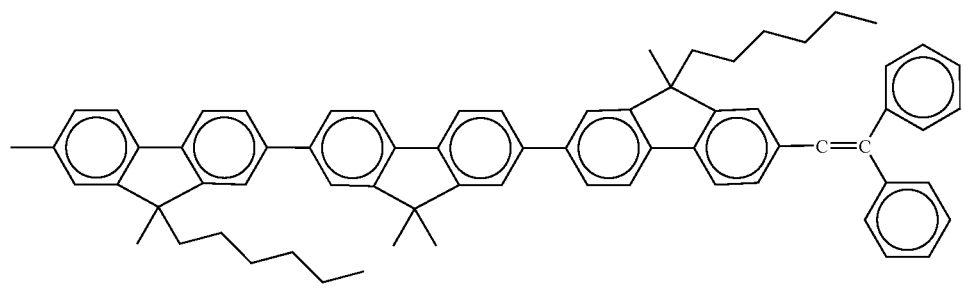
(A-20)
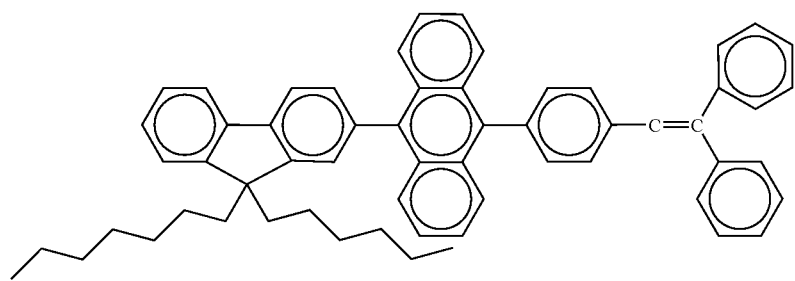
(A21)
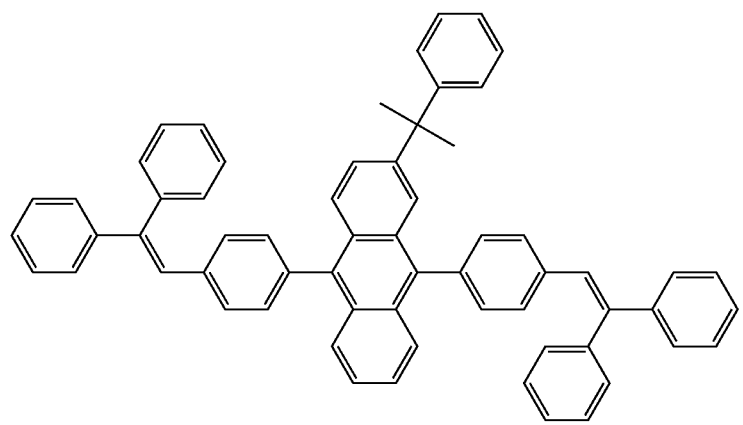

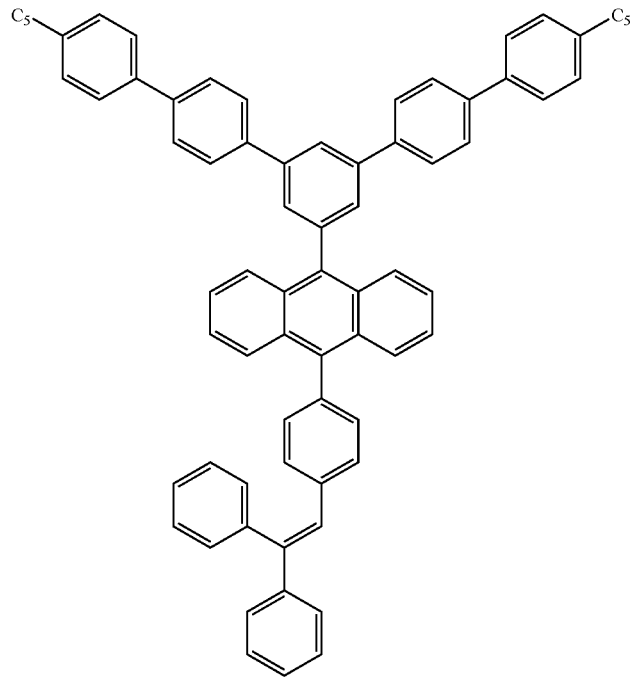

(A22)

The organic EL device of the present invention comprises a cathode, an anode and an organic thin film layer comprising a single layer or a plurality of layers and disposed between the cathode and the anode, and at least one layer in the organic thin film layer comprises the novel soluble compound described above.

It is preferable that, in the organic electroluminescence device which comprises a cathode, an anode and at least a light emitting layer and an electron transporting layer which are disposed between the cathode and the anode, the electron transporting layer comprises a novel soluble compound described above. It is also preferable that, in the organic electroluminescence device which comprises a cathode, an anode and at least a light emitting layer and a hole transporting layer which are disposed between the cathode and the anode, the hole transporting layer comprises a novel soluble compound described above.

It is preferable that the light emitting layer comprises an arylamine compound or a distyrylarylene derivative.

As the arylamine compound or the distyrylarylene derivative, it is preferable that a compound represented by the following general formula (2) or (3) is used.

General formula (2) is:

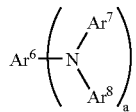

wherein $Ar^6$ represents an aromatic group having 6 to 40 carbon atoms, $Ar^7$ and $Ar^8$ each independently represent hydrogen atom or an aromatic group having 6 to 40 carbon atoms, the groups represented by $Ar^6$ to $Ar^8$ may be substituted, and a represents an integer of 1 to 6, which is the number of condensation.

General formula (3) is:

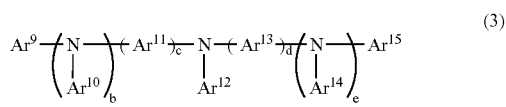

wherein $Ar^9$ and $Ar^{15}$ each represent an aromatic group having 6 to 40 carbon atoms, $Ar^{10}$ to $Ar^{14}$ each independently represent hydrogen atom or an aromatic group having 6 to 40 carbon atoms, the groups represented by $Ar^9$ to $Ar^{15}$ may be substituted, and b to e each represent 0 or 1, which is the number of condensation.

In general formulae (2) and (3) shown above, examples of the aromatic group having 6 to 40 carbon atoms include aryl groups such as phenyl group, naphthyl group, anthranyl group, phenanthryl group, pyrenyl group, coronyl group, biphenyl group, terphenyl group, pyrrolyl group, furanyl group, thiophenyl group, benzothiophenyl group, oxathiazolyl group, diphenylanthranyl group, indolyl group, carbazolyl group, pyridyl group, benzoquinolyl group, fluoranthenyl group and acenaphthofluoranthenyl group; and arylene groups such as phenylene group, naphthylene group, anthranylene group, phenanthrylene group, pyrenylene group, coronylene group, bip henylene group, terphenylene group, pyrrolylene group, furanylene group, thiophenylene group, benzothiophenylene group, oxadiazolylene group, diphenylanthranylene group, indolylene group, carbazolylene group, pyridylene group, benzoquinolylene group, fluoranthenylene group and acenaphtho-fluoranthenylene group. The aromatic group having 6 to 40 carbon atoms may be substituted. Examples of the substituent include alkyl groups having 1 to 6 carbon atoms such as ethyl group, methyl group, i-propyl group, n-propyl group, s-butyl group, t-butyl group, pentyl group, hexyl group, cyclopentyl group and cyclohexyl group; alkoxyl groups having 1 to 6 carbon atoms such as ethoxyl group, methoxyl group, i-propoxyl group, n-propoxyl group, s-butoxyl group, t-butoxyl group, pentoxyl group, hexyloxyl group, cyclopentoxyl group and cyclohexyloxyl group; aryl groups having a nucleus having 5 to 40 atoms; amino groups substituted with an aryl group having a nucleus having 5 to 40 atoms; ester groups having an aryl group having a nucleus having 5 to 40 atoms; ester groups having an alkyl group having 1 to 6 carbon atoms; cyano group; nitro group; and halogen atoms.

It is preferable that the light emitting layer comprises an aromatic cyclic compound having styryl group. Examples of the aromatic cyclic compound include N,N'-diphenyl-N,N'-bis(4-styrylphenyl)-1,4-diamino-naphthalene, N,N'-diphenyl-N,N'-bis(4-styrylphenyl)-1,4-diamino-2,3-dimethyl-naphthalene, N,N'-diphenyl-N,N'-bis(4-styrylphenyl)-3,8-diaminopyrene, N,N'-diphenyl-N,N'-bis(4-styrylphenyl)-9,10-diamino-anthracene and N,N'-diphenyl-N,N'-bis(4-styrylphenyl)-3,9-diamino perylene.

The organic EL device of the present invention has a laminate structure having one or more organic layers laminated between the electrodes. Examples of the structure include structures of an anode/a light emitting layer/a cathode, an anode/a hole transporting layer/a light emitting layer/an electron transporting layer/a cathode, an anode/a hole transporting layer/a light emitting layer/a cathode and an anode/a light emitting layer/an electron transporting layer/a cathode. The compound described in the present invention may be used in any of the above organic thin film layers and may also be used by doping into other hole transporting materials, light emitting materials and electron transporting materials.

The electron transporting material used for the electron transporting layer in the organic EL device of the present invention is not particularly limited, and compounds conventionally used as the electron transporting material can be used without particular restrictions. Examples of such compounds include oxadiazole derivatives and triazole derivatives such as 2-(4-biphenylyl)-5-(4-t-butylphenyl)-1,3,4-oxadiazole and bis{2-(4-t-butylphenyl)-1,3,4-oxadiazole}-m-phenylene and quinolinol-based metal complexes. As an inorganic compound constituting the electron transporting layer, insulating materials and semiconductors are preferable. When the electron transporting layer is constituted with the insulating material or the semiconductor, leak of electric current can be effectively prevented, and the electron injecting property can be improved. It is preferable that at least one metal compound selected from the group consisting of alkali metal chalcogenides, alkaline earth metal chalcogenides, alkali metal halides and alkaline earth metal halides is used as the insulating material. It is preferable that the electron transporting layer is constituted with the alkali metal chalcogenide or the like material since the electron injecting property can be further improved.

Examples of the alkali metal chalcogenide include $Li_2O$, LiO, $Na_2S$, $Na_2Se$ and NaO. Preferable examples of the alkaline earth metal chalcogenide include CaO, BaO, SrO, BeO, BaS and CaSe. Examples of the alkali metal halide include LiF, NaF, KF, LiCl, KCl and NaCl. Examples of the alkaline earth metal halide include fluorides such as $CaF_2$, $BaF_2$, $SrF_2$, $MgF_2$ and $BeF_2$ and halides other than the fluorides.

Examples of the semiconductor constituting the electron transporting layer include oxides, nitrides and oxide nitrides containing at least one element selected from Ba, Ca, Sr, Yb, Al, Ga, In, Li, Na, Cd, Mg, Si, Ta, Sb and Zn, which are used singly or as a combination of two or more. It is preferable that the inorganic compound constituting the electron transporting layer is in the form of a fine crystalline or amorphous insulating thin film. When the electron transporting layer is constituted with the above insulating thin film, a more uniform thin film can be formed and defective pixels such as dark spots can be decreased. Examples of the inorganic compound include the alkali metal chalcogenides, the alkaline earth metal chalcogenides, the alkali metal halides and the alkaline earth metal halides which are described above.

In the organic EL device of the present invention, it is preferable that a region transporting electrons or an interface region between the cathode and a layer of an organic thin film comprises a reducing dopant having a work function of 2.9 eV or smaller. The reducing dopant is defined as a substance which can reduce the electron transporting compound. Therefore, various types of substances can be used as long as the substance has the specific reducing property. For example, at least one substance selected from the group consisting of alkali metals, alkaline earth metals, rare earth metals, oxides of alkali metals, halides of alkali metals, oxides of alkaline earth metals, halides of alkaline earth metals, oxides of rare earth metals, halides of rare earth metals, organic complexes of alkali metals, organic complexes of alkaline earth metals and organic complexes of rare earth metals, can be used.

Specific examples of the reducing dopant include at least one alkali metal selected from the group consisting of Na (the work function: 2.36 eV), K (the work function: 2.28 eV), Rb (the work function: 2.16 eV) and Cs (the work function: 1.95 eV) and at least one alkaline earth metal selected from the group consisting of Ca (the work function: 2.9 eV), Sr (the work function: 2.0 to 2.5 eV) and Ba (the work function: 2.52 eV). Among these reducing dopants, reducing dopants having a work function of 2.9 eV or smaller are preferable. The more preferable reducing dopants are at least one alkali metal selected from the group consisting of K, Rb and Cs. The still more preferable reducing dopants are Rb and Cs, and the most preferable reducing dopant is Cs. These alkali metals have particularly great reducing ability, and the luminance of emitted light and the life of the organic EL device are improved by adding these alkali metals in a relatively small amount into the region of electron injection.

As the reducing dopant having a work function of 2.9 eV or smaller, combinations of two or more alkali metals are also preferable, and combinations including Cs such as combinations of Cs and Na, Cs and K, Cs and Rb, and Cs, Na and K are more preferable. When Cs is include in the combination, the reducing ability can be efficiently exhibited, and the luminance of emitted light and the life of the organic EL device can be improved by adding the combination into the region of electron injection.

The anode of the organic EL device plays the role of injecting holes into the hole transporting layer or the light emitting layer. It is effective that the anode has a work function of 4.5 eV or greater. Examples of the material of the anode used in the present invention include indium tin oxide alloys (ITO), tin oxides (NESA), gold, silver, platinum and copper. As the cathode, a material having a small work function is preferable so that electrons can be injected into the electron transporting layer or the light emitting layer. The material of the cathode is not particularly limited. Examples of the material of the cathode include indium, aluminum, magnesium, magnesium-indium alloys, magnesium-aluminum alloys, aluminum-lithium alloys, aluminum-scandium-lithium alloys and magnesium-silver alloys.

The process for forming the layers in the organic EL device of the present invention is not particularly limited. A conventional process such as the vacuum vapor deposition process and the spin coating process can be used.

The organic thin film layer comprising the compound represented by the above general formula (1) which is used in the organic EL device of the present invention can be formed in accordance with the vacuum vapor deposition process, the molecular beam epitaxy process (the MBE process) or, using a solution prepared by dissolving the compound into a solvent, in accordance with a conventional coating process such as the dipping process, the spin coating process, the casting process, the bar coating process and the roll coating process. In particular, the organic EL device exhibiting a great efficiency of light emission can be obtained in accordance with a wet process such as the spin coating process and the dipping process.

The thickness of each layer in the organic thin film layer in the organic EL device of the present invention is not particularly limited. In general, an excessively thin layer tends to have defects such as pin holes, and an excessively thick layer requires a high applied voltage to decrease the efficiency. Therefore, a thickness in the range of several nm to 1 µm is preferable.

The present invention will be described more specifically with reference to examples in the following. However, the present invention is not limited to the examples.

SYNTHESIS EXAMPLE 1

Synthesis of Compound (A1)

The route of synthesis of Compound (A1) (9,10-bis[4-(2, 2-diphenyl-ethenyl)phenyl]-2,6-di(2-ethylhexyloxy)anthracene) is shown in the following.

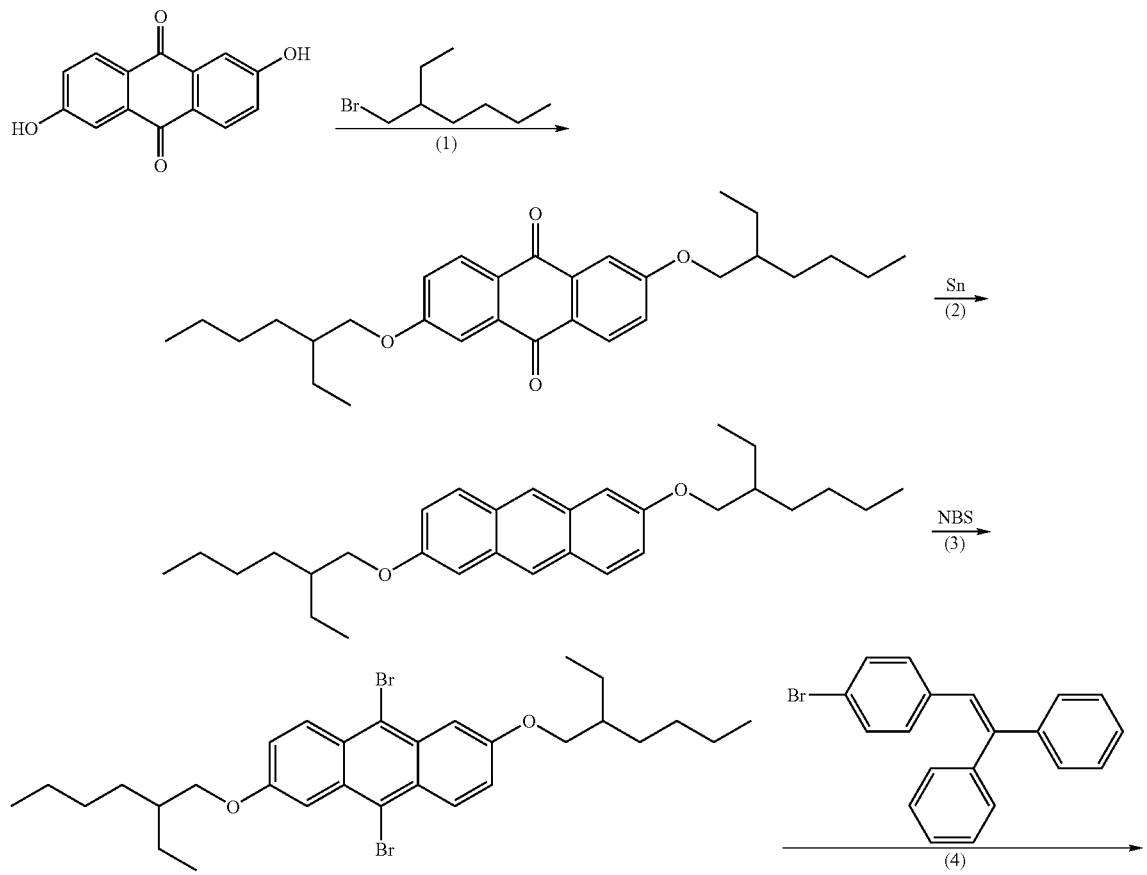

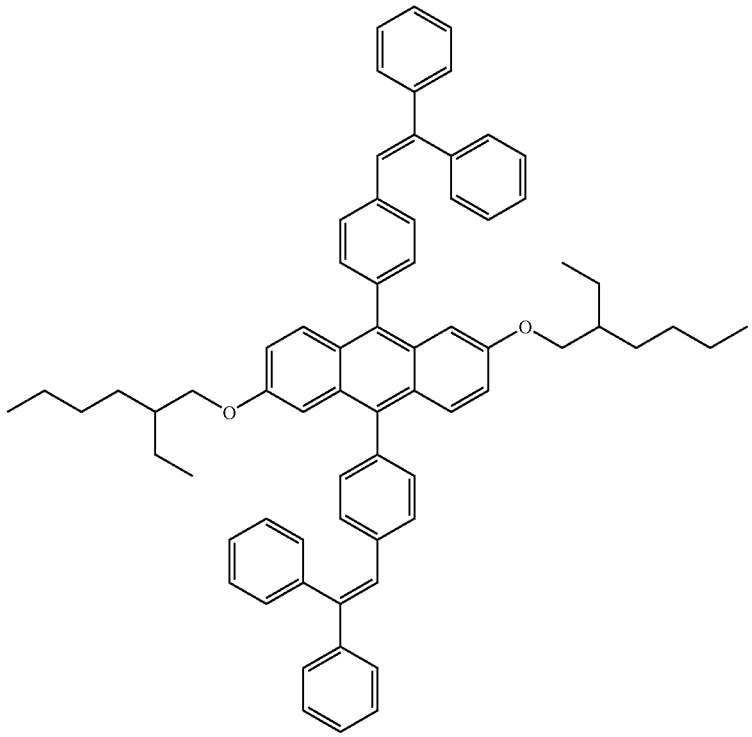

(A1)

(1) Synthesis of 2,6-di(2-ethylhexyloxy)anthraquinone

Into a 500 ml flask, 10 g (42 mmole) of 2,6-dihydroxyanthraquinone, 16.5 g (86 mmole) of 2-ethylhexyl bromide, 12 g (87 mmole) of anhydrous potassium carbonate and 200 ml of dimethylformamide (DMF) were placed, and the resultant mixture was heated at 90° C. under stirring for one night. After the reaction was completed, DMF was removed by distillation, and 50 ml of water was added. The reaction solution was treated by extraction with diethyl ether, washed with a saturated aqueous solution of sodium chloride and dried with magnesium sulfate. After the concentration under a reduced pressure, the obtained crude product was recrystallized from methanol, and 12.5 g of the quinone compound of the object compound was obtained (the yield: 65%; a yellow powder).

(2) Synthesis of 2,6-di(2-ethylhexyloxy)anthracene

Into a 200 ml flask, 7.5 g (16 mmole) of 2,6-di(2-ethylhexyloxy)-anthraquinone, 8 g (67 mmole) of tin and 37.5 ml of acetic acid were placed, and the resultant mixture was heated under the refluxing condition for 2 hours. After the reaction solution was cooled to the room temperature, the uppermost layer was separated by decantation, and the solid components were washed with methylene chloride. The obtained organic layers were combined, washed with water, a saturated aqueous solution of sodium hydrogencarbonate and a saturated aqueous solution of sodium chloride and dried with magnesium sulfate. After the solvent was removed, 7.2 g of a yellow solid was obtained.

In a 200 ml three-necked flask, the obtained yellow solid was dissolved into 20 ml of isopropyl alcohol (IPA). To the resultant solution, a solution prepared by dissolving 0.65 g (17 mmole) of $NaBH_4$ into 30 ml of IPA was slowly added dropwise, and the obtained solution was heated under stirring for one night. After the reaction was completed, water was added to the reaction solution. The formed precipitates were separated by filtration and washed with water and ethanol, and 5.5 g of the anthracene compound of the object compound was obtained (the yield: 78%; a yellow powder).

(3) Synthesis of 9,10-dibromo-2,6-di(2-ethylhexyloxy)anthracene

Into a 200 ml three-necked flask, 2.7 g (6 mmole) of 2,6-di(2-ethylhexyloxy)anthracene and 20 ml of DMF were placed and cooled to 0° C. To the obtained suspension, a solution prepared from 2.3 g (12 mmole) of N-bromosuccinimide (NBS) into 5 ml of DMF was slowly added dropwise, and the resultant mixture was stirred at the room temperature for one night. After the reaction was completed, the reaction solution was poured into 100 ml of water, and the resultant mixture was treated by extraction with methylene chloride. The organic layer was washed with a saturated solution of sodium hydrogencarbonate and a saturated solution of sodium chloride and dried with magnesium sulfate. After the concentration under a reduced pressure, the obtained dark brown residual product was purified in accordance with the silica gel chromatography (the developing solvent: hexane), and 1.1 g of the dibromo compound of the object compound was obtained (the yield: 30%; a yellow powder).

(4) Synthesis of 9,10-bis[4-(2,2-diphenylethenyl) phenyl]-2,6-di-(2-ethyl-hexyloxy)anthracene (Compound (A1))

Into a 500 ml three-necked flask equipped with a condenser, 0.16 g (6.6 mmole) of magnesium, a small piece of iodine and 10 ml of tetrahydrofuran (THF) were placed under a stream of argon. After the resultant mixture was stirred at the room temperature for 30 minutes, a solution prepared by dissolving 1 g (3 mmole) of 1-(4-bromophenyl)-2,2-diphenylethylene into 10 ml of THF was added dropwise. After the addition was completed, the resultant mixture was stirred at 60° C. for 1 hours, and a Grignard reagent was prepared.

Into a 500 ml flask equipped with a condenser, 0.6 g (1 mmole) of 9,10-dibromo-2,6-di(2-ethylhexyloxy)anthracene, 0.04 g (5% by mole) of dichlorobis(triphenylphosphine)palladium, 0.1 ml (1 M; 0.1 mmole) of a toluene solution of diusobutylaluminum hydride and 10 ml of THF were placed under a stream of argon. After the Grignard reagent prepared above was added dropwise to the obtained solution at the room temperature, the resultant mixture was heated under stirring for one night. After the reaction was completed, the reaction solution was cooled with ice water. The formed crystals were separated by filtration and washed with 50 ml of methanol and 50 ml of acetone successively, and 0.56 g of a yellow powder was obtained. The obtained yellow powder was identified to be Compound (A1) by the measurements in accordance with NMR, IR and the filed desorption mass spectroscopy (FD-MS) (the yield: 60%).

SYNTHESIS EXAMPLE 2

Synthesis of Compound (A2)

The route of synthesis of Compound (A2) (9,10-bis[4-(2,2-diphenyl-ethenyl)phenyl]-2,6/2,7-di-t-butylanthracene) is shown in the following.

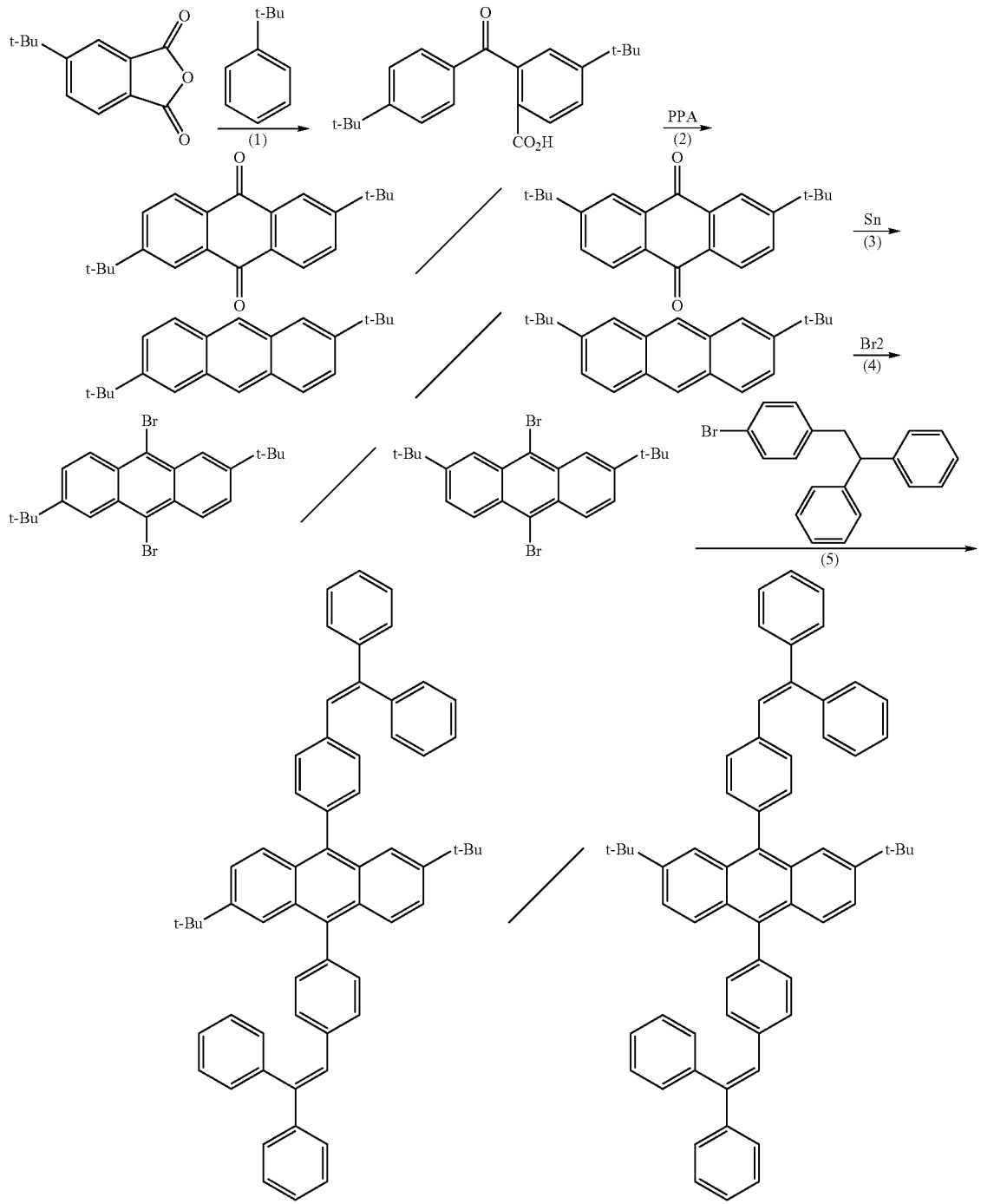

(A2)

(1) Synthesis of 4-t-butyl-2-(4-t-butylbenzoyl)benzoic acid

Into a 500 ml three-necked flask, 36 g (176 mmole) of 4-t-butyl-phthalic anhydride, 27 g (200 mmole) of t-butylbenzene and 100 ml of dichloroethane were placed under a stream of argon and cooled to 0° C. To the obtained mixture, 56 g (420 mmole) of aluminum chloride was slowly added. After the addition was completed, the resultant mixture was stirred at the room temperature for one night. After the reaction was completed, ice was added slowly, and then concentrated hydrochloric acid was added. The formed precipitates were separated by filtration and washed well with water, and 32 g of the benzoic acid compound of the object compound was-obtained (the yield: 54%; a white powder).

(2) Synthesis of 2,6/2,7-di-t-butylanthraquinone

Into a 500 ml flask having the egg plant shape equipped with a condenser, 200 ml of polyphosphoric acid was placed and heated at 150° C. Then, 32 g (95 mmole) of 4-t-butyl-2-(4-t-butylbenzoyl)benzoic acid was added in small portions, and the resultant mixture was stirred at the same temperature for 3 hours. After the reaction was completed, the reaction mixture was poured into ice water, and the resultant mixture was treated by liquid-liquid extraction with chloroform. After being dried with magnesium sulfate, the extract was concentrated under a reduced pressure by a rotary evaporator. The obtained crude crystals were recrystallized from hexane, and 21 g of the anthraquinone compound of the object compound was obtained (the yield: 69%; yellow crystals).

(3) Synthesis of 2,6/2,7-di-t-butylanthracene

Into a 300 ml flask, 10 g (313 mmole) of di-t-butylanthraquinone, 18 g (151 mmole) of tin and 50 ml of glacial acetic acid were placed, and the resultant mixture was heated under stirring. After the reaction was completed, the reaction solution was poured into ice water, and the resultant mixture was stirred for 30 minutes and treated by extraction with methylene chloride. After being dried with magnesium sulfate, the extract was concentrated under a reduced pressure by a rotary evaporator. The obtained oily solid substance was used for the reaction of the next step without purification.

In a 500 ml three-necked flask, the oily solid substance obtained above was dissolved into 110 ml of IPA. To the resultant solution, 13 g (333 mmole) of $NaBH_4$ was slowly added, and the obtained mixture was heated under stirring for one night. After the reaction was completed, water was added to the reaction solution. The formed precipitates were separated by filtration and washed with water and ethanol, and 8.8 g of the anthracene compound of the object compound was obtained (the yield: 97%; a yellow powder).

(4) Synthesis of 2,6/2,7-di-t-butyl-9,10-dibromoanthracene

Into a 300 ml flask, 4 g (13.8 mmole) of di-t-butylanthracene and 150 ml of carbon tetrachloride were placed, and 1.42 ml (27 mmole) of bromine was added dropwise. After the resultant mixture was stirred at the room temperature for one night, the reaction solution was poured into 200 ml of water, and the resultant mixture was treated by extraction with methylene chloride. The organic layer was washed with water, a saturated aqueous solution of sodium hydrogencarbonate and a saturated aqueous solution of sodium chloride and dried with magnesium sulfate. After the organic layer was concentrated under a reduced pressure, the obtained yellow solid was recrystallized from ethanol, and 6 g of the dibromoanthracene compound of the object compound was obtained (the yield: 97%; a yellow powder).

(5) Synthesis of 9,10-bis[4-(2,2-diphenylethenyl)phenyl]-2,6/2,7-di-t-butylanthracene (Compound (A2))

Into a 500 ml three-necked flask equipped with a condenser, 0.16 g (6.6 mmole) of magnesium, a small piece of iodine and 10 ml of THF were placed under a stream of argon. After the resultant mixture was stirred at the room temperature for 30 minutes, a solution prepared by dissolving 1 g (3 mmole) of 1-(4-bromophenyl)-2,2-diphenylethylene into 10 ml of THF was added dropwise. After the addition was completed, the resultant mixture was stirred at 60° C. for 1 hours, and a Grignard reagent was prepared.

Into a 500 ml three-necked flask equipped with a condenser, 0.45 g (1 mmole) of 2,6/2,7-di-t-butyl-9,10-dibromoanthracene, 0.04 g (5% by mole) of dichlorobis(triphenylphosphine)palladium, 0.1 ml (1M; 0.1 mmole) of a toluene solution of diisobutylaluminum hydride and 10 ml of THF were placed under a stream of argon. After the Grignard reagent prepared above was added dropwise to the obtained solution at the room temperature, the resultant mixture was heated under stirring for one night. After the reaction was completed, the reaction solution was cooled with ice water. The formed crystals were separated by filtration and washed with 50 ml of methanol and 50 ml of acetone successively, and 0.4 g of a yellow powder was obtained. The obtained yellow powder was identified to be Compound (A2) by the measurements in accordance with NMR, IR and FD-MS (the yield: 50%).

SYNTHESIS EXAMPLE 3

Synthesis of Compound (A21)

(1) Synthesis of 2-(2-phenyl-2-propyl)-9,10-bis(4-(2,2-diphenylvinyl)-phenyl)-9,10-dihydro-9,10-dihydroxyanthracene Under the atmosphere of argon, 4-(2,2-diphenylvinyl)bromobenzene (10 g, 30 mmole, 3 eq) was dissolved into a mixed solvent composed of anhydrous toluene (45 ml) and anhydrous THF (45 ml), and the resultant solution was cooled to −20° C. in a dry ice/methanol bath. To the cooled solution, a hexane solution of n-butyllithium (1.59 mmole/liter, 20 ml, 32 mmole, 1.06 eq) was added, and the obtained solution was stirred at −20° C. for 1 hour. To the resultant solution, 2-(2-phenyl-2-)propyl-anthraquinone (3.5 g, 11 mmole) was added, and the obtained mixture was stirred at the room temperature for 3 hours and then left standing for one night. To the resultant reaction mixture, a saturated aqueous solution of ammonium chloride (50 ml) was added. The organic layer was separated, washed with a saturated aqueous solution of sodium chloride and dried with magnesium sulfate. After the solvent was removed by distillation, the product was purified in accordance with the column chromatography (silica gel; hexane+50% dichloromethane, dichloromethane and finally dichloromethane+3% methanol), and a light yellow amorphous solid was obtained (5.7 g; the yield: 67%).

(2) Synthesis of 2-(2-phenyl-2-propyl)-9,10-bis(4-(2,2-diphenylvinyl)-phenyl)anthracene (Compound (A21))

2-(2-Phenyl-2-propyl)-9,10-bis(4-(2,2-diphenylvinyl)phenyl)-9,10-dihydro-9,10-dihydroxyanthracene (5.7 g, 6.7 mmole), potassium iodide (3.3 g, 20 mmole) and sodium phosphinate monohydrate (1.1 g, 10 mmole) were dissolved into acetic acid (50 ml), and the resultant solution was stirred at 100° C. The reaction mixture was diluted with water (50 ml) and treated by extraction with toluene (300 ml). The organic layer was washed with a saturated aqueous solution of sodium chloride (50 ml) and dried with magnesium sulfate. After the solvent was removed by distillation, the obtained product was purified in accordance with the column chromatography (silica gel; hexane+30% dichloromethane), and a light yellow solid was obtained (4.5 g; 82%). The obtained product was identified to be Compound (A21) by the measurements in accordance with $^1$H-NMR and FD-MS.

SYNTHESIS EXAMPLE 4

Synthesis of Compound (A22)

(1) Synthesis of Compound 1

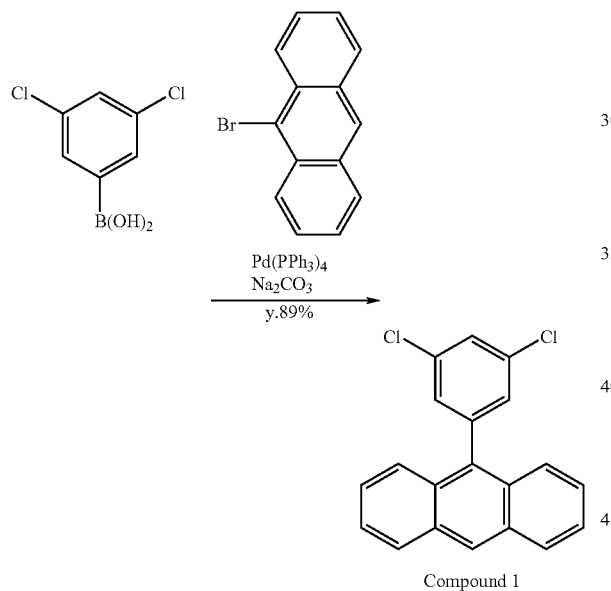

Compound 1

Into a three-necked flask, 3,5-dichlorobenzene-1-boronic acid (3.0 g), 9-bromoanthracene (4.47 g) and Pd(PPh$_3$)$_4$ (0.54 g) were placed, and the system was purged with argon. To the resultant mixture, toluene (20 ml) and an aqueous solution (2.4 ml) of sodium carbonate (5.02 g) were added, and the obtained mixture was heated under the refluxing condition for 7 hours. The reaction solution was treated by extraction with toluene, and the extract was concentrated under a reduced pressure. The obtained solid was washed with ethanol, and Compound 1 was obtained (the amount of the product: 4.52 g; the yield: 89%).

$^1$H-NMR (CDCl$_3$): δ (ppm) 8.51 (s,1H), 8.2-8.0 (m, 2H), 7.8-7.0 (m, 9H)

(2) Synthesis of Compound 2

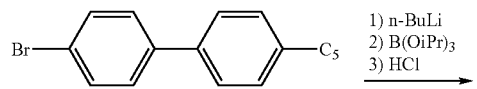

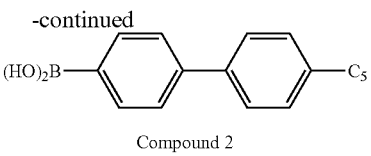

Compound 2

Into a flask purged with argon, 4-bromo-4'-n-pentylbiphenyl (5.0 g) and anhydrous ether (50 ml) were placed and cooled to −20° C. To the cooled solution, a 1.6 M hexane solution (15.2 ml) of n-butyllithium was slowly added dropwise. After 30 minutes, the temperature was elevated to the room temperature, and the mixture was stirred at the room temperature for 1 hour. The obtained reaction solution was added dropwise into an anhydrous ether solution (80 ml) of triisopropyl borate (8.28 g) at −20° C. The temperature was elevated to the room temperature, and the reaction solution was stirred for one night. To the resultant reaction solution, 2N hydrochloric acid was added, and the obtained mixture was stirred for 1 hour. The organic layer was separated and concentrated under a reduced pressure. The obtained solid was purified in accordance with the silica gel column chromatography (the solvent for elution: hexane/ethyl acetate=3/1, 2/1 and 0/1 used in this order), and Compound 2 was obtained (the amount of the product: 1.77 g; the yield: 40%).

$^1$H-NMR (CDCl$_3$): δ (ppm) 8.3 (d, 1H), 7.9-7.5 (m, 6H), 7.3 (m, 1H), 4.6 (s, 2H), 2.6 (t, 2H), 1.8-1.2 (t, 6H), 0.9 (t, 3H)

(3) Synthesis of Compound 3

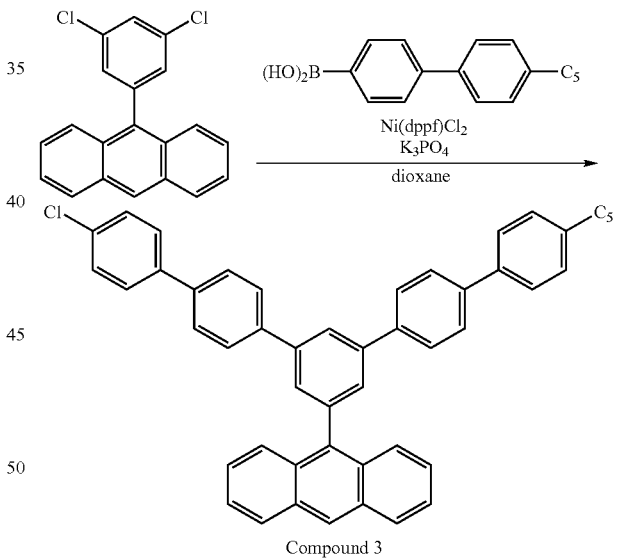

Compound 3

Into a three-necked flask purged with argon, Compound 1 (0.75 g), Compound 2 (1.50 g), Ni(dppf)Cl$_2$ (64 mg), tripotassium phosphate (2.84 g) and dioxane (20 ml) were placed, and the resultant mixture was heated under the refluxing condition for 11 hours. To the reaction solution, water (100 ml) was added, and a solid was separated. The separated solid was washed with ethanol and purified in accordance with the silica gel column chromatography (the solvent for elution: hexane/methylene chloride=4/1), and Compound 3 was obtained (the amount of the product: 0.80 g; the yield: 49%).

$^1$H-NMR (CDCl$_3$): δ (ppm) 8.6 (s, 1H), 8.2-7.2 (m, 27H), 2.6 (t, 2H), 1.8-1.2 (m, 6H), 0.9 (t, 3H)

(4) Synthesis of Compound 4

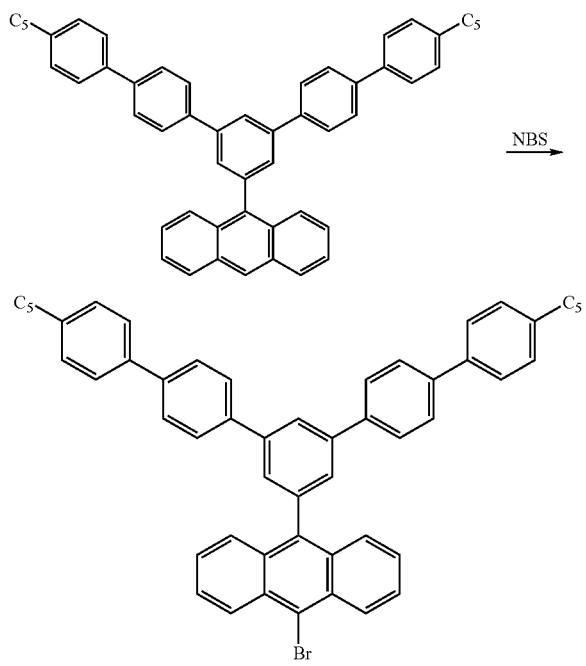

Compound 4

Compound 3 (0.80 g) was dissolved into N,N-dimethylformamllide (20 ml). N-bromosuccinimide (0.24 g) was added, and the resultant solution was stirred at the room temperature for one day. The obtained solution was treated by extraction by adding water (100 ml) and methylene chloride (100 ml), and the obtained organic layer was washed with 1 N hydrochloric acid (twice each with 50 ml).

The organic layer was concentrated under a reduced pressure. The obtained solid was purified in accordance with the silica gel column chromatography (the solvent for elution: hexane/methylene chloride=1/1), and Compound 4 was obtained (the amount of the product: 0.98 g; the yield: 110%). Although Compound 4 contained N,N-dimethylformamide, Compound 4 was used for the reaction in the next step without further treatments.

$^1$H-NMR (CDCl$_3$): δ (ppm) 8.6 (d, 1H), 8.2-7.2 (m, 27H), 2.7 (t, 2H), 1.8-1.2 (m, 6H), 0.9 (t, 3H)

(5) Synthesis of 9-(4-(2,2-diphenylvinyl)phenyl)-10-(3,5-bis(4-pentyl-phenyl)phenyl)phenylanthracene (A22)

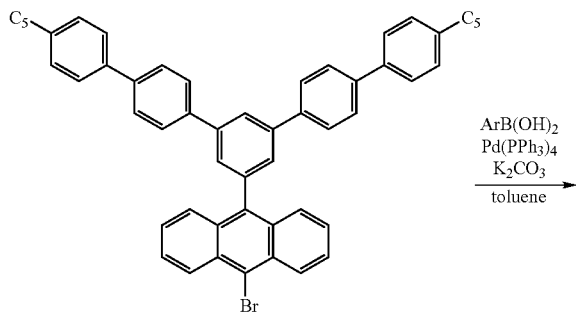

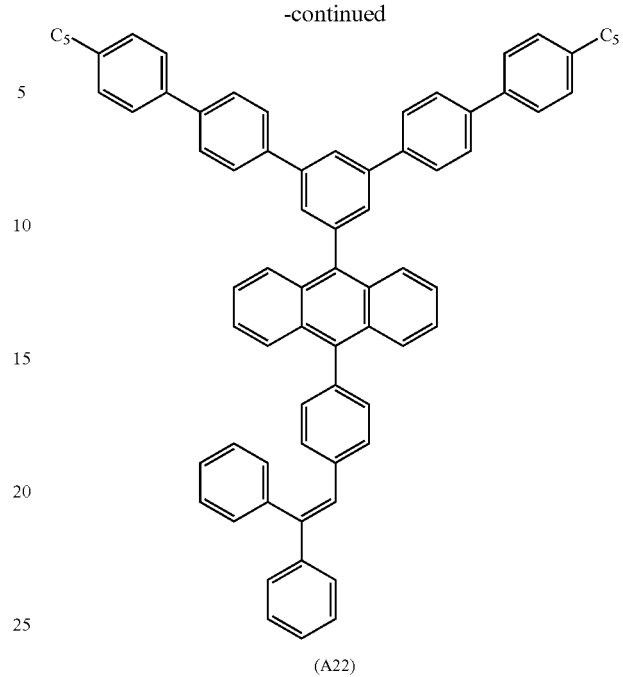

(A22)

Into a flask, Compound 4 (0.98 g), 4-(2,2-diphenylethenyl)phenyl-boric acid (0.41 g) and Pd(PPh$_3$)$_4$ (40 mg) were placed under the atmosphere of argon. To the resultant mixture, toluene (10 ml) and an aqueous solution (1.7 ml) of sodium carbonate (0.37 g) were added, and the obtained mixture was heated at 80° C. for 6.5 hours. The reaction mixture was treated by extraction by adding water (100 ml) and methylene chloride (100 ml), and the organic layer was concentrated under a reduced pressure. The obtained solid was purified in accordance with the silica gel column chromatography (the solvent for elution: hexane), and Compound (A22) was obtained (the amount of the product: 0.86 g; the yield: 78%).

$^1$H-NMR (CDCl$_3$): δ (ppm) 8.0-7.2 (m, 39H), 2.6 (t, 2H), 1.8-1.2 (m, 6H), 0.9 (t, 3H)

EXAMPLE 1

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode lines, a light emitting layer was formed using a dichloroethane solution (1.5% by weight) containing 2 parts by weight of Compound (A1) and 1 part by weight of an arylamine compound shown below in accordance with the spin coating process. The formed light emitting layer had a thickness of 120 nm. On the formed light emitting layer, a film of tris(8-quinolinol)aluminum (Alq film) having a thickness of 10 nm was formed. The Alq film worked as the electron injecting layer. Thereafter, Li (the source of lithium: manufactured by SAES GETTERS Company) as the reducing dopant and Alq were binary vapor deposited, and an Alq:Li film was formed as the electron injecting layer (the cathode). On the formed Alq:Li film, metallic aluminum was vapor deposited to form a metal cathode, and an organic EL device was prepared. The obtained device emitted bluish green light with a luminance of 150 cd/m² under application of a direct voltage of 7 V, and the efficiency of light emission was as excellent as 2.67 lumen/W.

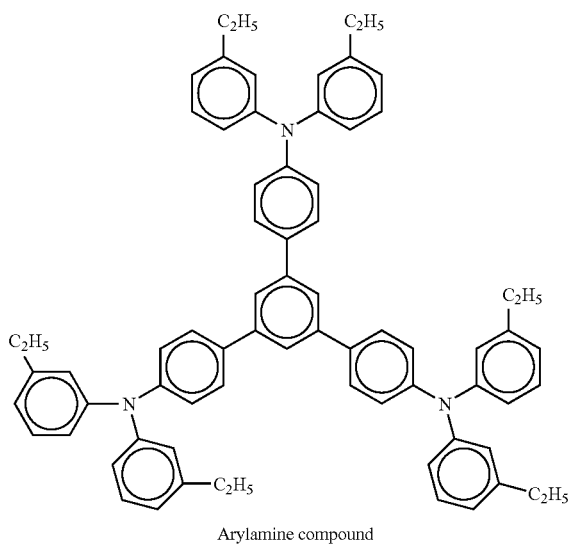

Arylamine compound

EXAMPLES 2 TO 8

Organic EL devices were prepared in accordance with the same procedures as those conducted in Example 1 except that compounds shown in Table 1 were used in place of Compound (A1) used in Example 1. The luminance of the emitted light, the efficiency of light emission and the color of the emitted light exhibited by the prepared devices under application of a direct voltage of 6 V are shown in Table 1.

TABLE 1

| | Compound | Voltage (V) | Luminance of emitted light (cd/m²) | Efficiency of light emission (lumen/W) | Color of emitted light |
|---|---|---|---|---|---|
| Example 2 | (A2) | 6 | 130 | 1.94 | blue |
| Example 3 | (A7) | 6 | 161 | 2.34 | blue |
| Example 4 | (A9) | 6 | 95 | 1.02 | blue |
| Example 5 | (A10) | 6 | 210 | 2.56 | blue |
| Example 6 | (A14) | 6 | 120 | 1.87 | bluish green |
| Example 7 | (A17) | 6 | 115 | 1.13 | blue |
| Example 8 | (A20) | 6 | 313 | 2.65 | bluish green |

As shown in Table 1, the organic EL devices in Example 2 to 8 exhibited excellent efficiencies of light emission. This result was obtained since the novel soluble compound comprising the distyrylarylene derivative of the present invention used in the light emitting layer had the specific central group having a soluble substituent.

COMPARATIVE EXAMPLE 1

An organic EL devices was prepared in accordance with the same procedures as those conducted in Example 1 except that the following compound described in Japanese Patent Application Laid-Open No. 2000-143589:

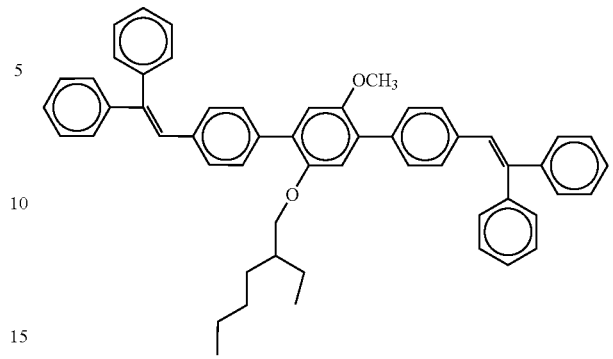

was used in place of Compound (A1) used in Example 1. The obtained device exhibited an efficiency of light emission under application of a direct voltage of 6 V of 0.81 lumen/W, which was markedly smaller than those in Examples.

COMPARATIVE EXAMPLE 2

In the same procedures as those conducted in Example 1, 4,4″-bis(2,2-diphenylethenyl)-9',10'-diphenylanthracene was used in place of Compound (A1) and attempted to be dissolved in organic solvents, which were toluene, xylene, N-methylpyrrolidone, γ-butyrolactone, 1,3-dimethyl-2-imidazoline, carbitol acetate, butylcarbitol acetate, dichloromethane, dichloroethane, chlorobenzene and isopropyl alcohol. However, this compound was hardly soluble in these solvents since the solubility was smaller than 0.01% by weight in all of these solvents, and no device could be prepared.

EXAMPLE 9

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode lines, a light emitting layer was formed using a dichloroethane solution (2% by weight) containing 4 parts by weight of Compound (A1) and 1 part by weight of a styrylamine compound shown below in accordance with the spin coating process. The formed light emitting layer had a thickness of 130 nm. On the formed light emitting layer, a film of tris(8-quinolinol)aluminum (Alq film) having a thickness of 10 nm was formed. The Alq film worked as the electron injecting layer. Thereafter, Li (the source of lithium: manufactured by SAES GETTERS Company) as the reducing dopant and Alq were binary vapor deposited, and an Alq:Li film was formed as the electron injecting layer (the cathode). On the formed Alq:Li film, metallic aluminum was vapor deposited to form a metal cathode, and an organic EL device was prepared. The obtained device emitted bluish green light with a luminance of 250 cd/m² under application of a direct voltage of 7 V, and the efficiency of light emission was as excellent as 1.91 lumen/W.

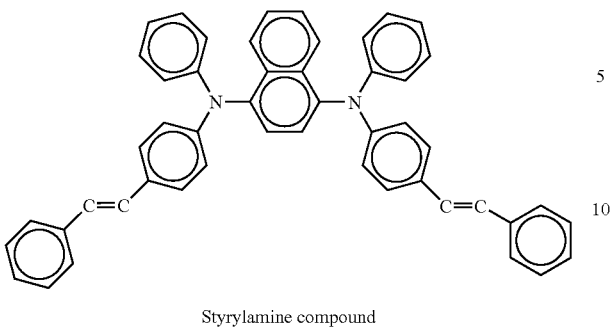

Styrylamine compound

INDUSTRIAL APPLICABILITY

As described above in detail, the organic EL device exhibiting a great efficiency of light emission can be produced easily by utilizing the novel soluble compound of the present invention since the organic thin film layer can be formed in accordance with the wet process.

Therefore, the organic electroluminescence device of the present invention is very useful as the inexpensive light source for various electronic instruments.

The invention claimed is:

1. A novel soluble compound that is a distyrylarylene derivative represented by general formula (1) and has a solubility (20° C.) of 0.5% by weight or greater in an organic solvent, general formula (1) being:

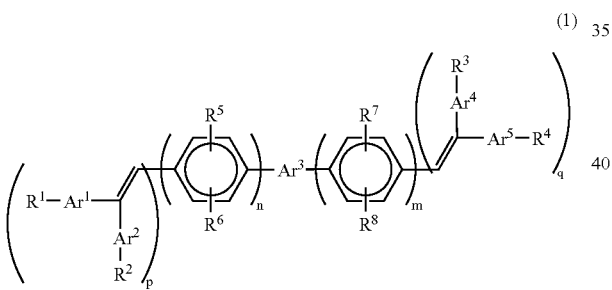

(1)

wherein $Ar^1$, $Ar^2$, $Ar^4$ and $Ar^5$ each independently represent a substituted or unsubstituted phenylene group, a substituted or unsubstituted naphthalene group, a substituted or unsubstituted anthracene group, a substituted or unsubstituted diphenylanthracene group, a substituted or unsubstituted phenanthrene group, a substituted or unsubstituted acenaphthene group, a substituted or unsubstituted biphenylene group, a substituted or unsubstituted fluorene group, a substituted or unsubstituted carbazolyl group, a substituted or unsubstituted thiophene group, a substituted or unsubstituted triazole group or a substituted or unsubstituted thiadiazole group;

$R^1$ to $R^4$ each independently represent hydrogen atom, an alkyl group having 1 to 20 carbon atoms, an alkoxyl group having 1 to 20 carbon atoms, an aryl group having 6 to 20 carbon atoms, a trialkylsilyl group having 3 to 20 carbon atoms or cyano group;

$Ar^3$ represents a fluorendiyl group comprising:
at least one substituent group selected from:
(a) linear and branched alkyl groups having 5 or more carbon atoms and an olefinic unsaturated bond,
(b) linear, branched and cyclic substituted alkyl groups having 4 or more carbon atoms,
(c) linear, branched and cyclic substituted alkyloxyl groups having 5 or more carbon atoms,
(d) linear, branched and cyclic substituted alkylthio groups having 5 or more carbon atoms,
(e) linear, branched and cyclic substituted alkylsilyl groups having 5 or more carbon atoms,
(f) linear, branched and cyclic substituted dialkylsilyl groups having 5 or more carbon atoms,
(g) linear, branched and cyclic substituted trialkylsilyl groups having 5 or more carbon atoms,
(h) linear and branched cyano-substituted alkyl groups having 4 or more carbon atoms and 1 or 2 cyano groups, and
(i) polyethers having 2 to 5 ether oxygen atoms which are separated from each other with an alkyl crosslinking having 1 to 3 carbon atoms, or a fluorendiyl group comprising a substituent group selected from: aryl groups having 6 to 30 carbon atoms, arylalkyl groups having 7 to 30 carbon atoms, heteroarylalkyl groups having at least one nitrogen atom, oxygen atom and sulfur atom and 2 to 30 carbon atoms, heterocyclic groups having 2 to 30 carbon atoms, alkanoyl groups having 1 to 20 carbon atoms; cycloalkanoyl groups having 6 to 30 carbon atoms, aryloyl groups having 6 to 30 carbon atoms, and heteroaryloxyl groups having at least one oxygen atom and sulfur atom and 2 to 30 carbon atoms, wherein the substituent is itself substituted with at least one group selected from aforesaid (a) to (i); and excluding a case where the fluorendiyl group is substituted with two benzene rings;

$R^5$ to $R^8$ each independently represent hydrogen atom, a halogen atom, hydroxyl group, a substituted or unsubstituted amino group, nitro group, cyano group, a substituted or unsubstituted alkyl group having 1 to 30 carbon atoms, a substituted or unsubstituted alkenyl group having 2 to 30 carbon atoms, a substituted or unsubstituted cycloalkyl group having 5 to 30 carbon atoms, a substituted or unsubstituted alkoxyl group having 1 to 30 carbon atoms, a substituted or unsubstituted aromatic hydrocarbon group having 6 to 30 carbon atoms, a substituted or unsubstituted aromatic heterocyclic group having 2 to 30 carbon atoms, a substituted or unsubstituted aralkyl group having 7 to 30 carbon atoms, a substituted or unsubstituted aryloxyl group having 6 to 30 carbon atoms, a substituted or unsubstituted alkoxycarbonyl group having 2 to 30 carbon atoms or carboxyl group, groups represented by $R^6$ and $R^5$ or $R^7$ and $R^8$ may be bonded to each other and form a cyclic structure which may have substituents;

p represents 0 or 1, q represents 0 or 1, m represents 0 or an integer of 1 to 3, and n represents an integer of 1 to 3, wherein at least one of $R^5$ to $R^8$ represents at least one group selected from:
(1) linear and branched alkyl groups having 5 or more carbon atoms and an olefinic unsaturated bond,
(2) linear, branched and cyclic substituted and unsubstituted alkyl groups having 4 or more carbon atoms,
(3) linear, branched and cyclic substituted and unsubstituted alkyloxyl groups having 5 or more carbon atoms,
(4) linear, branched and cyclic substituted and unsubstituted alkylthio groups having 5 or more carbon atoms, (5) linear, branched and cyclic substituted and unsubstituted alkylsilyl groups having 5 or more carbon atoms,
(6) linear, branched and cyclic substituted and unsubstituted dialkylsilyl groups having 5 or more carbon atoms,
(7) linear, branched and cyclic substituted and unsubstituted trialkylsilyl groups having 5 or more carbon atoms,
(8) alkylamino groups and dialkylamino groups,
(9) linear and branched cyano-substituted alkyl groups having 4 or more carbon atoms and 1 or 2 cyano groups, and
(10) polyethers having 2 to 5 ether oxygen atoms which are separated from each other with an alkyl crosslinking having 1 to 3 carbon atoms, or a group selected from aryl groups having 6 to 30 carbon atoms, arylalkyl groups having 7 to 30 carbon atoms, heteroarylalkyl groups having at least one of nitrogen atom, oxygen atom and sulfur atom and 2 to 30 carbon atoms, heterocyclic groups having 2 to 30 carbon atoms, alkanoyl groups having 1 to 20 carbon atoms, cycloalkanoyl groups having 6 to 30 carbon atoms, aryloyl groups having 6 to 30 carbon atoms and heteroaryloxyl groups having at least one of oxygen atom and sulfur atom and 2 to 30 carbon atoms, which are substituted with at least one group selected from aforesaid (1) to (10).

2. A novel soluble compound according to claim 1, wherein the organic solvent is at least one solvent selected from toluene, xylene, N-methylpyrrolidone, γ-butyrolactone, 1,3-dimethyl-2-imidazoline, carbitol acetate, butylcarbitol acetate, dichloromethane, dichloroethane, chloro-benzene and alcohols having 1 to 10 carbon atoms.

3. An organic electroluminescence device which comprises a cathode, an anode and an organic thin film layer comprising a single layer or a plurality of layers and disposed between the cathode and the anode, wherein at least one layer in the organic thin film layer comprises a novel soluble compound described in claim 1.

4. An organic electroluminescence device which comprises a cathode, an anode and at least a light emitting layer and an electron transporting layer which are disposed between the cathode and the anode, wherein the electron transporting layer comprises a novel soluble compound described in claim 1.

5. An organic electroluminescence device which comprises a cathode, an anode and at least a light emitting layer and a hole transporting layer which are disposed between the cathode and the anode, wherein the hole transporting layer comprises a novel soluble compound described in claim 1.

6. An organic electroluminescence device according to claim 3, wherein the organic thin film layer is formed in accordance with a wet process.

7. An organic electroluminescence device according to claim 4, wherein the light emitting layer is formed in accordance with a wet process.

8. An organic electroluminescence device according to claim 5, wherein the light emitting layer is formed in accordance with a wet process.

9. An organic electroluminescence device according to claim 4, wherein the light emitting layer comprises an arylamine compound.

10. An organic electroluminescence device according to claim 5, wherein the light emitting layer comprises an arylamine compound.

11. An organic electroluminescence device according to claim 4, wherein the light emitting layer comprises an aromatic cyclic compound having styryl group.

12. An organic electroluminescence device according to claim 5, wherein the light emitting layer comprises an aromatic cyclic compound having styryl group.

* * * * *